United States Patent
Dairiki

[11] Patent Number: 5,974,890
[45] Date of Patent: *Nov. 2, 1999

[54] COMPOSITE PROBE APPARATUS

[75] Inventor: Kenichi Dairiki, Tokyo, Japan

[73] Assignee: Mitsubishi Denki Kabushiki Kaisha, Tokyo, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/708,460

[22] Filed: Sep. 5, 1996

[30] Foreign Application Priority Data

Nov. 27, 1995 [JP] Japan ................................ 7-307867

[51] Int. Cl.$^6$ ........................... G01N 29/10; G01N 29/24
[52] U.S. Cl. ................................. 73/625; 73/632; 73/641
[58] Field of Search ........................... 73/632, 641, 625, 73/624, 626, 642, 644; 310/322, 366, 334, 336, 338, 365, 328; 128/660.01

[56] References Cited

U.S. PATENT DOCUMENTS

| | | | |
|---|---|---|---|
| 2,628,335 | 2/1953 | Drake | 73/625 |
| 3,847,016 | 11/1974 | Ziedonis | 73/632 |
| 4,254,661 | 3/1981 | Kossoff et al. | 73/625 |
| 4,944,191 | 7/1990 | Pastrone et al. | |
| 5,376,857 | 12/1994 | Takeuchi et al. | 310/328 |
| 5,398,216 | 3/1995 | Hall et al. | 367/90 |
| 5,431,054 | 7/1995 | Reeves et al. | 73/641 |

FOREIGN PATENT DOCUMENTS

| | | |
|---|---|---|
| 0620434 | 10/1994 | European Pat. Off. . |
| 3442751A1 | 6/1986 | Germany . |
| 58-33501 | 7/1983 | Japan .............................. G01N 29/04 |
| 07218485 | 8/1995 | Japan . |

OTHER PUBLICATIONS

M. Pappalardo "Hybrid Linear and Matrix Acoustic Arrays" Ultrasonic, Mar. 1981.

*Primary Examiner*—Hezron Williams
*Assistant Examiner*—Rose M. Miller
*Attorney, Agent, or Firm*—Burns, Doane, Swecker & Mathis, LLP

[57] ABSTRACT

A composite probe apparatus exhibiting a high performance and a high efficiency in detecting internal defects of a steel pipe or a steel plate, coupled with offering a stable sensitivity and covering a wide range for flaw detection. A plurality of reception oscillators PR1 to PR4 are disposed in a zigzag fashion in both sides of a transmission oscillator PT. The length 1 T of the transmission oscillator PT is determined such that a near sound field is established over the entire measuring range, while the width WT of the transmission oscillator PT is determined such that a far sound field takes place over the entire measuring range. The transmission and reception oscillators are constructed with a common piezoelectric plate an electrode of which undergoes division.

4 Claims, 4 Drawing Sheets

COMPOSITE PROBE APPARATUS

BACKGROUND OF THE INVENTION

1. Field of the Invention

The present invention relates to a composite probe apparatus available for an ultrasonic detection of flaws or cracks being internal defects of a steel plate or a steel pipe.

2. Description of the Related Art

FIG. 4 is an explanatory illustration of an ultrasonic flaw detector using a prior composite vertical probe disclosed by the Japanese Examined Patent Publication No. 58-33501. In FIG. 4, character T represents a pulse transmitter, character PT designates a transmission oscillator, characters PR1 to PR3 denote reception oscillators, character DT depicts a transmission delaying member, character DR signifies a reception delaying member, character SP indicates a transmission and reception ultrasonic wave separating plate, character TP shows a material under examination, character RS stands for a reception input switch, character R means a reception amplifier, character F shows an internal defect of the material TP under examination, character 1 T indicates a dimension of the transmission oscillator, a dotted line 1 designates a defective ultrasonic echo path propagating from the transmission oscillator PT to the reception oscillators PR1 to PR3.

In the prior ultrasonic flaw detector, a plurality of reception oscillators PR1 to PR3 are disposed in parallel to the one transmission oscillator PT, and the transmission oscillator PT generates periodic ultrasonic attenuating vibration in response to the supply of a periodic pulse electric output from the pulse transmitter T. A transmission ultrasonic beam propagating in the material TP under examination covers a range (width) slightly smaller than the transmission oscillator dimension T and advances through the transmission delaying member DT into the material TP under examination as indicated by the dotted line 1. Thereafter, the transmission ultrasonic beam is reflected at the internal defect F of the material TP under examination to proceed through the reception delaying member DR to the reception oscillators PR1 to PR3. Moreover, the transmission ultrasonic beams received by the reception oscillators PR1 to PR3 are piezoelectric-transduced into electric signals which in turn, are received by the reception amplifier R after passing through the reception input switch RS, thereby measuring the defect dimension on the basis of the echo level corresponding to the defect F.

In the case of this prior flaw detector, one of the reception oscillators PR1 to PR3, which is positioned to assume the shortest propagation distance from the position of the defect F in the oscillator width direction, receives the defect echo level with a high sensitivity. However, when the defect F lies between the reception oscillators PR1 and PR2, the echo from the defect F is dispersedly received by the reception oscillators PR1 and PR2, and hence the reception sensitivity lowers so that difficulty is encountered to ensure uniform sensitivity among the composite oscillators.

One solution to this problem is that the two successive reception oscillators PR1 and PR2 are simultaneously turned on through the reception input switch RS to receive the echo in parallel. However, the reception oscillator width is doubled to cause the sensitivity to lower and the defect detecting ability lowers because of the increase in the circuit loss of the reception input switch PR. Furthermore, according to this method, when for example the oscillators PR2 and PR3 receive the echo during the reception period of the oscillators PR1 and PR2, the middle oscillator PR2 comes into an overlapped condition so that the uniform sensitivity performance is unobtainable. For this reason, two kinds of signals are received in a time-sharing mode. On the other hand, in the case of an automatic flaw detecting apparatus in an iron and steel line where the material TP under examination moves at a high speed, accompanying the lengthening of the defect F echo reception period, this method signifies making the defect F data obtaining pitch rough or making the scanning speed low, thus lowering the defect detection performance, giving rise to great scattering of the defect detection sensitivity and impairing of the processing ability. That is, since difficulty is experienced in ensuring a uniform sensitivity and a wide effective beam width with one composite probe, the prior method requires a plurality of probes in order to ensure a wide beam width.

The plurality of probes can not be disposed on the same line in the beam width direction because of the restriction of dimension and hence they are required to be disposed in a zigzag fashion such that the separations between the probes in the direction of the transmission and reception oscillators exceed the dimension of the probes. However, this is accompanied by the increase in the dimension and weight of the probe holding device, and in the case of an apparatus such as an iron and steel line thick-plate automatic flaw detector which searches for flaws while the probe holding device follows the vertical movements of the material TP under examination, a problem exists in that the zigzag-disposed probes defy complete scanning of the material TP under examination, with the result that the range of the non-detected plate end portions enlarges, and the probe scanning device becomes complicated with increased cost.

SUMMARY OF THE INVENTION

The present invention has been developed with a view to eliminating these problems, and it is therefore an object of the present invention to provide a composite probe apparatus which is capable of obtaining a wide effective beam width, of permitting less performance deterioration, and of disposing probes in a row.

In a composite probe apparatus according to this invention, a transmission oscillator is disposed at a central portion while reception oscillators are located in a zigzag fashion at both sides of the transmission oscillator so that the zigzag-fashioned reception oscillators are partially overlapped with each other.

Furthermore, in a composite probe apparatus according to this invention, its dimensions are determined so that the near sound field takes place within the material under examination in the direction parallel to the transmission and reception division direction of the transmission oscillator disposed at its central portion and so that the far sound field is taken within the material under examination in the direction perpendicular thereto.

Moreover, in a composite probe apparatus according to this invention, the transmission and reception oscillators are formed by dividing an electrode on a common piezoelectric plate.

Still further, in a composite probe apparatus according to this invention, a transmission and reception ultrasonic wave separating plate is located in a transmission and reception division plane between the transmission oscillator and the reception oscillators and in a plane confronting the front surface of a material under examination.

BRIEF DESCRIPTION OF THE DRAWINGS

The object and features of the present invention will become more readily apparent from the following detailed description of the preferred embodiments taken in conjunction with the accompanying drawings in which.

DESCRIPTION OF THE PREFERRED EMBODIMENTS

First Embodiment

Figure 1:
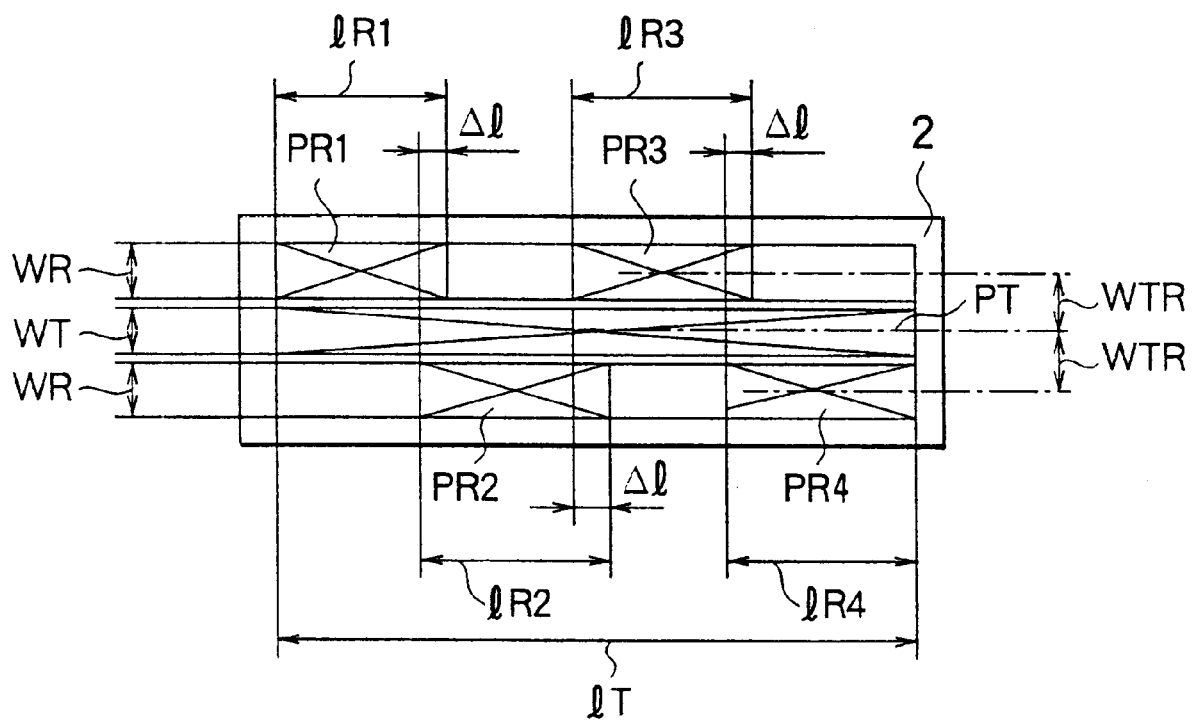
FIG. 1 is an illustration of an arrangement of oscillators of a composite probe apparatus according to a first embodiment of the present invention.
Figure 2A:
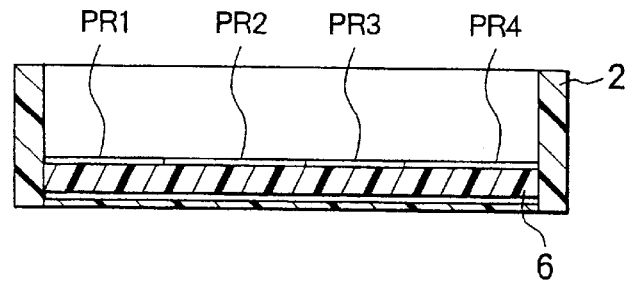
FIGS. 2A to 2C are illustrations of a cross section of the composite probe apparatus according to the first embodiment of this invention, and of reception patterns.
Figure 2B:
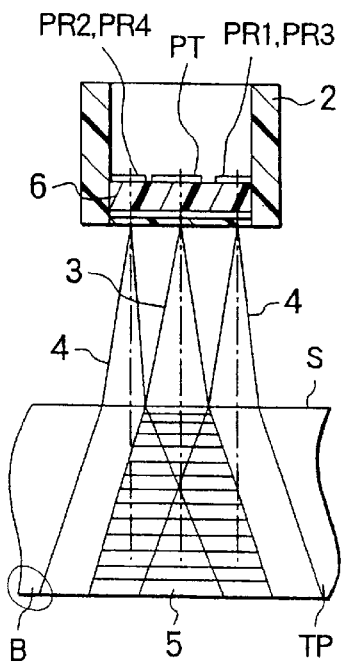
Figure 2C:
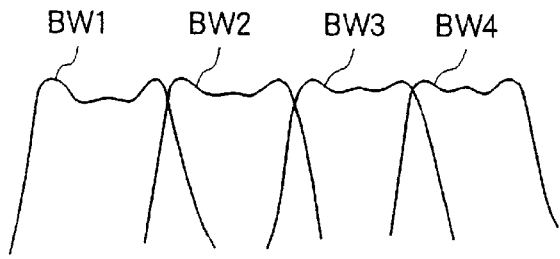

FIG. 1 shows a disposition of oscillators of a composite probe apparatus according to a first embodiment of the present invention, FIG. 2A illustrates a cross section of the composite probe apparatus parallel to a transmission and reception division direction, FIG. 2B shows a cross section thereof perpendicular to the transmission and reception division direction, and FIG. 2C is an illustration of an ultrasonic wave reception pattern formed with reception oscillators disposed in a zigzag fashion.

In these illustrations, numeral 2 represents a probe case, numeral 3 designates an ultrasonic beam emitted from a transmission oscillator PT, numeral 4 denotes ultrasonic beams to reception oscillators PR1 to PR4, numeral 5 signifies a receivable region in which the transmission ultrasonic beam 3 is overlapped with the ultrasonic beams 4 to the reception oscillators PR1 to PR4, numeral 6 depicts a common piezoelectric plate, character PT indicates a transmission oscillator, characters PR1 to PR4 stand for reception oscillators, character TP shows a material being examined, character S denotes a front or top surface of the material TP under examination, and character B depicts a bottom surface of the material TP under examination.

Further, character l T represents the length of the transmission oscillator PT parallel to a transmission and reception division direction, characters l R1 to l R4 respectively designate the lengths of the reception oscillators PR1 to PR4 in directions parallel to the corresponding transmission and reception division directions, character Δl denotes the overlapping dimensions of the reception oscillators PR1 and PR2, the reception oscillators PR2 and PR3, and the reception oscillators PR3 and PR4 which are disposed in a zigzag fashion, character WT denotes the width of the transmission oscillator PT perpendicular to the transmission and reception division direction, character WR signifies widths of the reception oscillators PR1 to PR4 normal to the transmission and reception division direction, character WTR indicates the spacing between the transmission oscillator PT and the reception oscillators PR1, PR3 or the reception oscillators PR2, PR4, and characters BW1 to BW4 denote reception patterns formed with the reception oscillators PR1 to PR4 disposed in a zigzag fashion.

In the composite probe apparatus thus constructed, since the length T of the transmission oscillator PT is determined so that the near sound field critical distance ($X_0 = l\,T^2/4\lambda$, where $\lambda$ denotes a wavelength) is greater than the maximum thickness of the material TP under examination, the effective beam width in the direction of the transmission oscillator PT length l T becomes slightly smaller than the length l T of the transmission oscillator PT, and the beam substantially advances in parallel from the front or top surface S to the bottom surface B of the material TP under examination.

In both sides of the transmission oscillator PT, the reception oscillators PR1 to PR4 are disposed to be overlapped with each other in a range of 10 to 20% of their lengths l R1 to l R4 to form the overlapping portions Δl, with the result that no gap between the beam patterns BW1 to BW4 is produced by the reception oscillators PR1 to PR4 in the direction parallel to the transmission and reception division direction, thus offering a uniform characteristic.

Further, the width WT of the transmission oscillator PT, the width WR of the reception oscillators PR1 to PR4 and the spacing WTR between the transmission oscillator PT and the reception oscillators PR1 to PR4 in the direction perpendicular to the transmission and reception division direction are set so that the ultrasonic beam 3 from the transmission oscillator PT is sufficiently overlapped with the ultrasonic beams 4 to the reception oscillators PR1 to PR4 within the material TP under examination, where WTR≦2× tan (the directional angle of the transmission oscillator PT dimension)×the distance from the piezoelectric plate 6 to the top surface S of the material TP under examination. Accordingly, the receivable region 5 can be taken in a wide range from the top surface S to the bottom surface B of the material TP under examination.

Moreover, the transmission oscillator PT and the reception oscillators PR1 to PR4 are not constructed with individual parts but are constructed with the piezoelectric plate provided in common thereto. Thus, the transmission oscillator PT and the reception oscillators PR1 to PR4 are formed by dividing the electrode on the piezoelectric plate 6, and housed in the probe case 2. For this reason, the components can have the same structure as the general one-oscillator type probe except drawing out lead lines.

The prior composite probe apparatus is required to separate the ultrasonic delaying members DT and DR by the transmission and reception ultrasonic wave separating plate SP in order to prevent the leakage of the ultrasonic wave. Since this separating plate SP is required to be disposed in a state that it is brought close to the top surface S of the material TP under examination in a range below 0.5 mm therefrom, it can come into contact with projections on the top surface S of the material TP under examination or foreign matters to undergo damages or abrasion so that the flaw detection performance deteriorates. In addition, the maintenance and inspection are troublesome. On the other hand, according to the first embodiment of this invention, there is no need to set up the transmission and reception ultrasonic separating plate SP, and thus it is possible to eliminate this disadvantage.

Second Embodiment

Figure 3A:
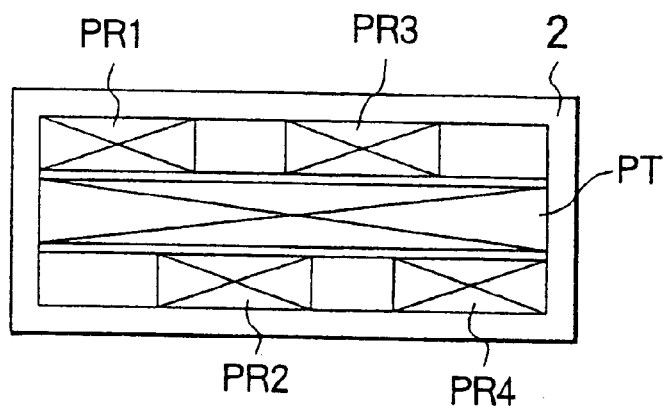
FIGS. 3A and 3B are illustrations of a construction of a composite probe apparatus according to a second embodiment of this invention.
Figure 3B:
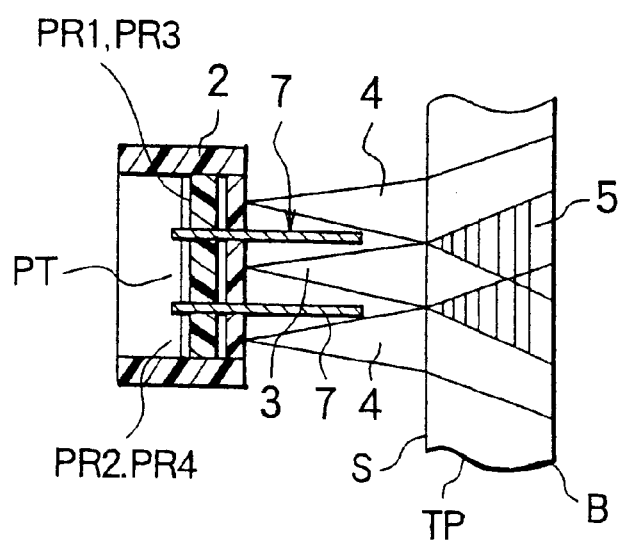
Figure 4:
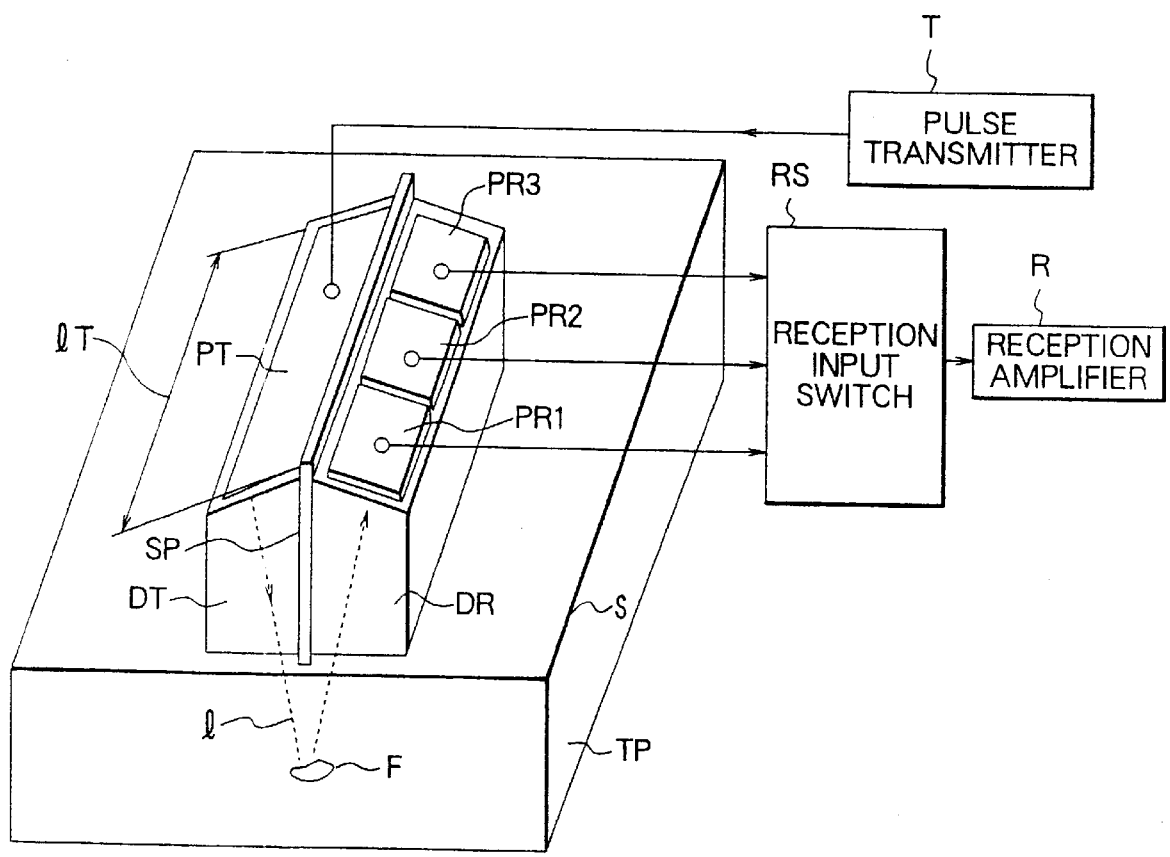
FIG. 4 is an illustration of an ultrasonic flaw detector using a prior composite vertical probes.

FIGS. 3A and 3B are cross-sectional views showing a composite probe apparatus according to a second embodiment of this invention. In the illustrations, numeral 2 represents a probe case, numeral 3 designates an ultrasonic beam transmitted from a transmission oscillator PT, numeral 4 denote ultrasonic beams to reception oscillators PR1 to PR4, numeral 5 depicts a receivable region where the transmission ultrasonic beam is overlapped with the ultrasonic beams to the reception oscillators PR1 to PP4, numeral 7 signifies transmission and reception ultrasonic wave separating plates placed in division planes between the transmission oscillator PT and the reception oscillators PR1 to PR4, character PT indicates the transmission oscillator, characters PR1 to PR4 show the reception oscillators, character TP stands for a material under examination, character S represents a top surface of the material TP under examination, and character B denotes a bottom surface of the material TP under examination.

In the composite probe apparatus thus constructed, the transmission and reception ultrasonic wave separating plates 7 are provided in the division planes between the transmission oscillator PT and the reception oscillators PR1, PR3 and the reception oscillators PR2, PR4 and in the planes facing the top surface S of the material TP under examination. Thus, the ultrasonic beam emitted from the transmission oscillator PT reaches the top surface S of the material TP under examination and a portion of the ultrasonic beam 3 is reflected on the top surface S of the material TP under examination to be received by the reception oscillators PR1 to PR4. At this time, the components of the ultrasonic beam 3 on the top surface S of the material TP under examination, which have a high sound pressure, are shut off by the transmission and reception ultrasonic wave separating plates 7 when being reflected to the reception oscillators PR1 to PR4. In consequence, the ultrasonic beams reflected from the front surface S of the material TP under examination and reaching the reception oscillators PR1 to PR4 are left as only the components whose sound pressures are low, thus creating a weak surface echo.

As described above, according to this invention, the reception oscillators are disposed in a zigzag fashion in both sides of the transmission oscillator and the zigzag-fashioned reception oscillators are arranged to be partially overlapped with each other, and thus no gaps between beam patterns formed by the respective reception oscillators in the direction parallel to the transmission and reception division direction occur so that a uniform beam characteristic is obtainable, with the result that it is possible to surely detect defects existing within the effective width of the beam from the transmission oscillator PT. In addition, the spacings between the zigzag-fashioned reception oscillators in the direction perpendicular to the transmission and reception division direction are small, so that it is possible to reduce the non-detected region in the front and rear end portions of the material TP under examination.

Furthermore, according to this invention, since the oscillator length in the direction parallel to the transmission and reception division direction of the transmission oscillator is determined so that the near sound field lies over the entire measuring range, the transmission ultrasonic beam becomes a parallel beam substantially equal to the oscillator length in the ultrasonic wave propagation distance direction.

In addition, since the oscillator width in the direction normal to the transmission and reception division direction is determined so that the far sound field occurs throughout the entire measuring range, the reception oscillators disposed in both the sides of the transmission oscillator can receive the beams with a sufficient sensitivity, and the widths of the transmission oscillator and the reception oscillators and the spacings between the transmission oscillator and the reception oscillators are optimized so that it is possible to reduce the surface echo inherent in the two-oscillator probe and it is possible to provide a probe which defies its performance deterioration for a long period of time.

Moreover, according to this invention, since the common piezoelectric plate is used and the transmission oscillator and the reception oscillators are formed only by dividing the electrode section, there is no need to take positioning and assembling of the oscillators into consideration and to finely process the oscillators using a processing machine such as a dicing saw, which can provide a probe apparatus with a stable characteristic at a low cost.

Still further, according to this invention, since the transmission and reception ultrasonic wave separating plates are provided in the transmission and reception division plane between the transmission oscillator and the reception oscillators located in both sides of the transmission oscillator and in the plane confronting the front surface of the material under examination, it is possible to lowering the surface echo level on the flaw detection figure, with the result that it is possible to provide a probe apparatus which is capable of improving the defect detecting ability with respect to the vicinity of the surface of the material under examination.

It should be understood that the foregoing relates to only preferred embodiments of the present invention, and that it is intended to cover all changes and modifications of the embodiments of the invention herein used for the purposes of the disclosure, which do not constitute departures from the spirit and scope of the invention.

What is claimed is:

1. A composite probe apparatus, comprising:
   at least one transmission oscillator configured to transmit an ultrasonic wave, each of said at least one transmission oscillators having a first side, a second side and a length extending along said first and second sides;
   at least one first reception oscillator configured to receive a reflected ultrasonic wave and positioned at at least one first location along said length of one of said at least one transmission oscillator on said first side of said one of said at least one transmission oscillator; and
   at least one second reception oscillator configured to receive the reflected ultrasonic wave and positioned at least one second location along said length of one of said at least one transmission oscillator on said second side of said one of said at least one transmission oscillator;
   wherein said at least one first location is different than said at least one second location and wherein a length of one of said at least one first reception oscillator and a length of one of said at least one second reception oscillator are partially overlapped in an area along a longitudinal direction of the one of said at least one transmission oscillator.

2. The composite probe apparatus as defined in claim 1, wherein the at least one transmission oscillator is configured to produce ultrasound having a near sound field lying over a measuring range of a material under examination, and wherein the at least one transmission oscillator is configured to produce ultrasound having a far sound field occurring throughout the entire measuring range.

3. The composite probe apparatus as defined in claim 1, wherein the at least one transmission oscillator and the at least one first and at least one second reception oscillators are formed by dividing an electrode on a common piezoelectric plate.

4. The composite probe apparatus as defined in claim 1, further comprising two separating plates, a first of said separating plates disposed between one of said at least one transmission oscillator and the at least one first reception oscillator and a second of said separating plates disposed between said one of said at least one transmission oscillator and the at least one second reception oscillator.

* * * * *